(12) United States Patent
Wine et al.

(10) Patent No.: US 12,036,380 B2
(45) Date of Patent: Jul. 16, 2024

(54) NEEDLELESS CONNECTOR WITH COMPRESSIBLE AND DEFLECTABLE VALVE

(71) Applicant: CareFusion 303, Inc., San Diego, CA (US)

(72) Inventors: Jason Andrew Wine, Placentia, CA (US); George Mansour, Diamond Bar, CA (US)

(73) Assignee: CAREFUSION 303, INC., San Diego, CA (US)

( * ) Notice: Subject to any disclaimer, the term of this patent is extended or adjusted under 35 U.S.C. 154(b) by 512 days.

(21) Appl. No.: 17/307,630

(22) Filed: May 4, 2021

(65) Prior Publication Data
US 2022/0355095 A1    Nov. 10, 2022

(51) Int. Cl.
*A61M 39/26*    (2006.01)
*A61M 39/10*    (2006.01)

(52) U.S. Cl.
CPC ............ *A61M 39/26* (2013.01); *A61M 39/10* (2013.01)

(58) Field of Classification Search
CPC .............................. A61M 39/10; A61M 39/26
See application file for complete search history.

(56) References Cited

U.S. PATENT DOCUMENTS

| | | | |
|---|---|---|---|
| 5,690,612 A * | 11/1997 | Lopez | A61M 5/14 604/246 |
| 5,782,816 A * | 7/1998 | Werschmidt | A61M 39/02 251/149.6 |
| 8,840,577 B1 * | 9/2014 | Zollinger | A61M 39/22 604/167.03 |
| 9,089,682 B2 * | 7/2015 | Yeh | A61M 39/10 |

(Continued)

FOREIGN PATENT DOCUMENTS

| | | | |
|---|---|---|---|
| EP | 3659669 A1 | 6/2020 | |
| WO | WO-2011014265 A1 * | 2/2011 | ............ A61M 39/10 |

OTHER PUBLICATIONS

International Search Report and Written Opinion for Application No. PCT/US2022/026577, dated Sep. 28, 2022, 20 pages.

(Continued)

*Primary Examiner* — Nathan R Price
*Assistant Examiner* — Mark A Igel
(74) *Attorney, Agent, or Firm* — Morgan, Lewis & Bockius LLP

(57) ABSTRACT

A needleless connector may include a housing having a proximal end, a distal end, and an inner surface defining an internal cavity extending between the proximal and distal ends. A compressible valve may be disposed within the internal cavity. The compressible valve may include a head portion, a flange portion for securing the compressible valve in the housing, and a body portion extending between the head portion and the flange portion. The body portion may (Continued)

include a cylindrical outer surface having an external notch extending along a portion of a circumference of the cylindrical outer surface and recessed radially-inward from the cylindrical outer surface. The body portion may further include a planar face extending distally from the external notch and disposed between the external notch and the flange portion. The planar face may be recessed radially inward relative to at least a portion of the cylindrical outer surface.

15 Claims, 9 Drawing Sheets

(56) References Cited

U.S. PATENT DOCUMENTS

| | | | |
|---|---|---|---|
| 2001/0049508 A1* | 12/2001 | Fangrow, Jr. | A61M 39/045 |
| | | | 604/167.01 |
| 2003/0208165 A1* | 11/2003 | Christensen | A61M 39/26 |
| | | | 264/494 |
| 2010/0308251 A1* | 12/2010 | Pascal | A61M 39/26 |
| | | | 251/324 |
| 2011/0028914 A1* | 2/2011 | Mansour | A61M 39/22 |
| | | | 604/246 |
| 2013/0030386 A1* | 1/2013 | Panian | A61M 39/26 |
| | | | 29/890.12 |
| 2013/0060205 A1* | 3/2013 | Mansour | A61M 39/223 |
| | | | 604/500 |
| 2014/0135709 A1* | 5/2014 | Zollinger | A61M 39/20 |
| | | | 604/246 |
| 2014/0276463 A1* | 9/2014 | Mansour | A61M 39/22 |
| | | | 604/256 |
| 2014/0276466 A1* | 9/2014 | Yeh | A61M 39/26 |
| | | | 604/256 |
| 2016/0158524 A1* | 6/2016 | Quach | A61M 39/22 |
| | | | 604/256 |
| 2016/0325085 A1* | 11/2016 | Chelak | F16K 7/20 |
| 2018/0015278 A1* | 1/2018 | Ueda | A61M 39/26 |
| 2019/0232043 A1* | 8/2019 | Truitt | A61M 39/1011 |
| 2022/0339423 A1* | 10/2022 | Weber | A61M 39/18 |

OTHER PUBLICATIONS

Invitation to Pay Additional Fees and Partial International Search Report for Application No. PCT/US2022/026577, dated Aug. 4, 2022, 14 pages.

* cited by examiner

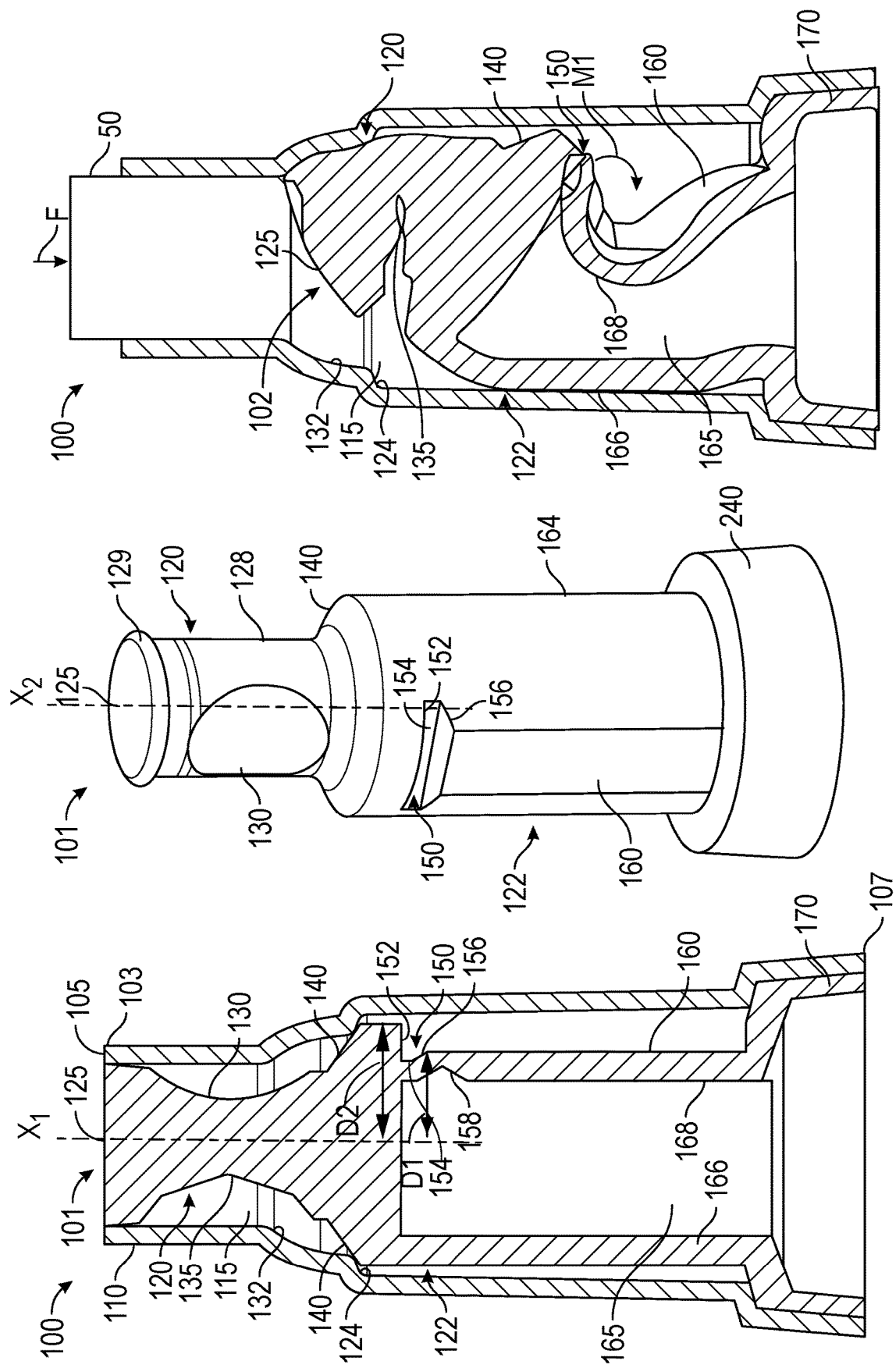

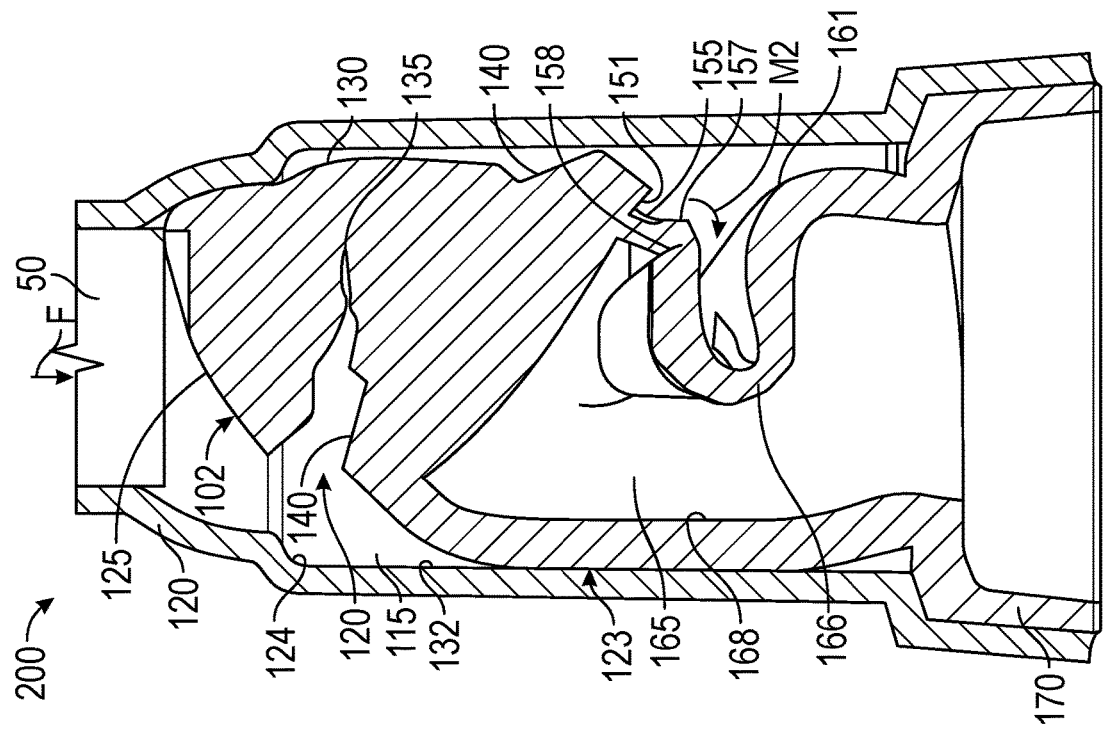
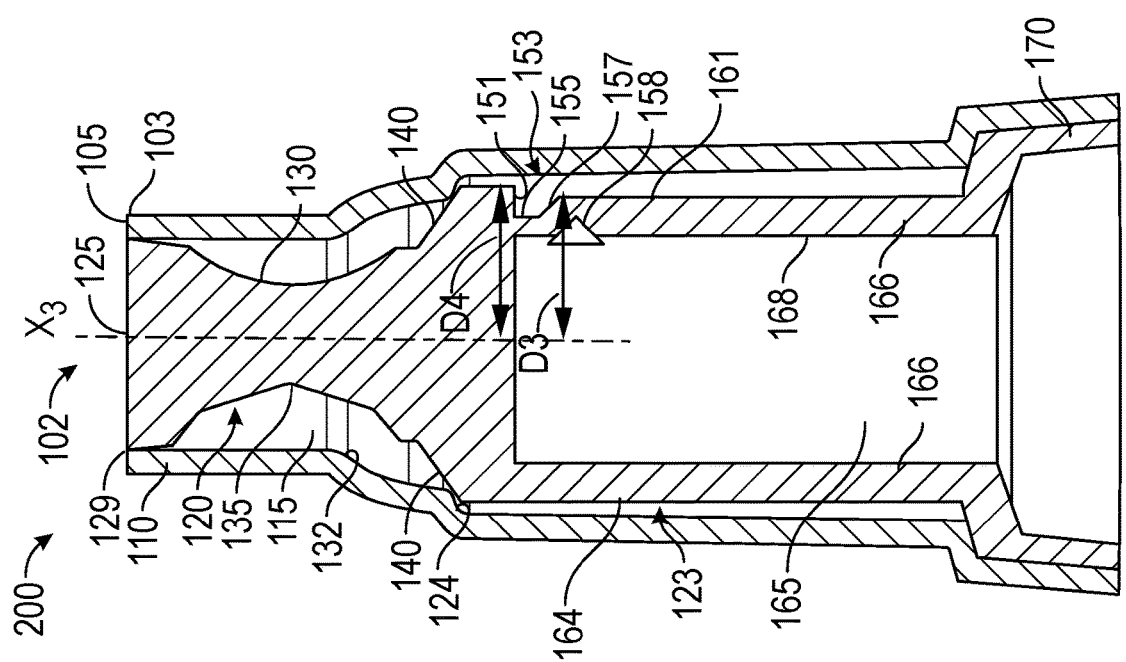
FIG. 3A
FIG. 3B

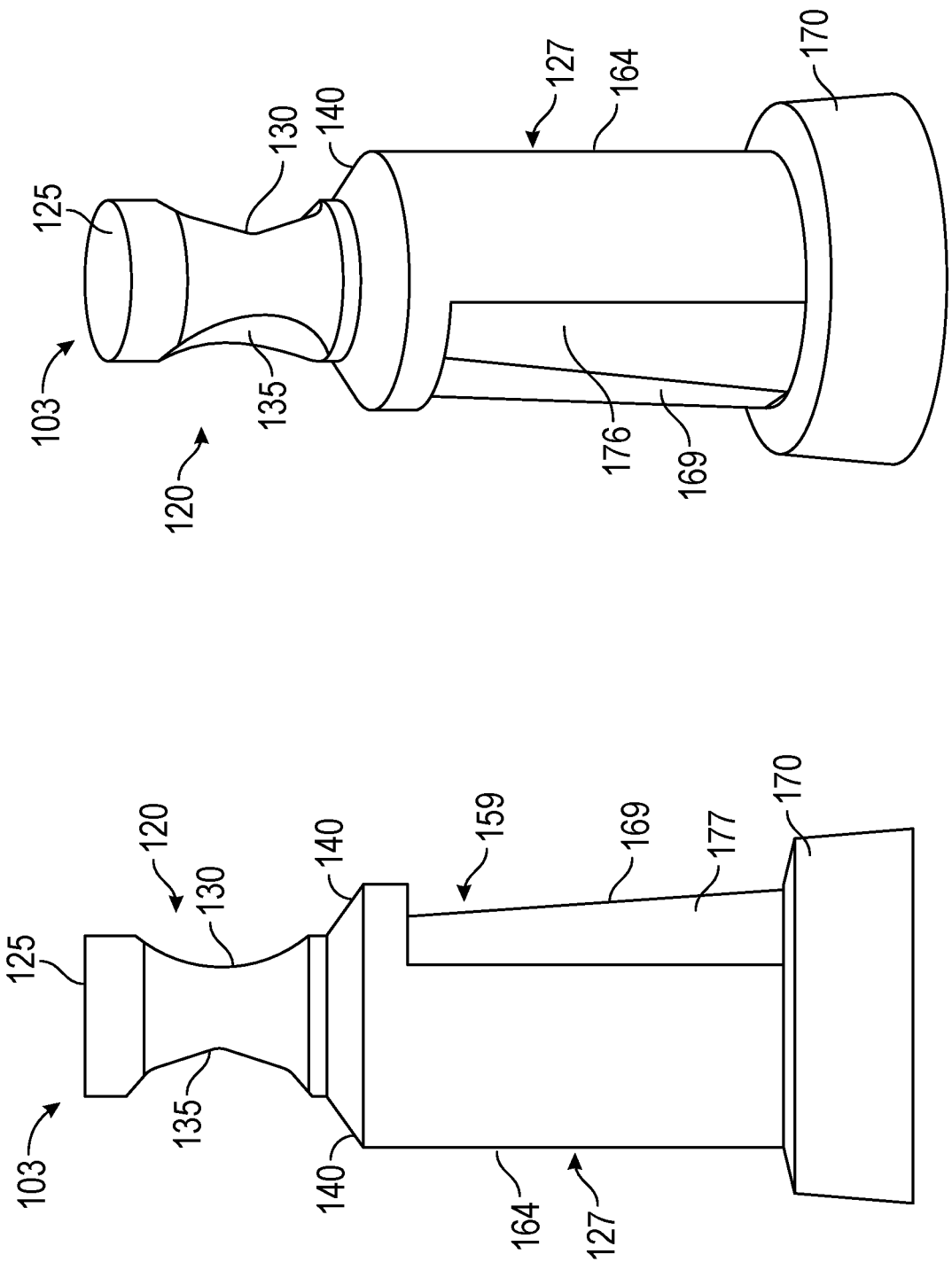

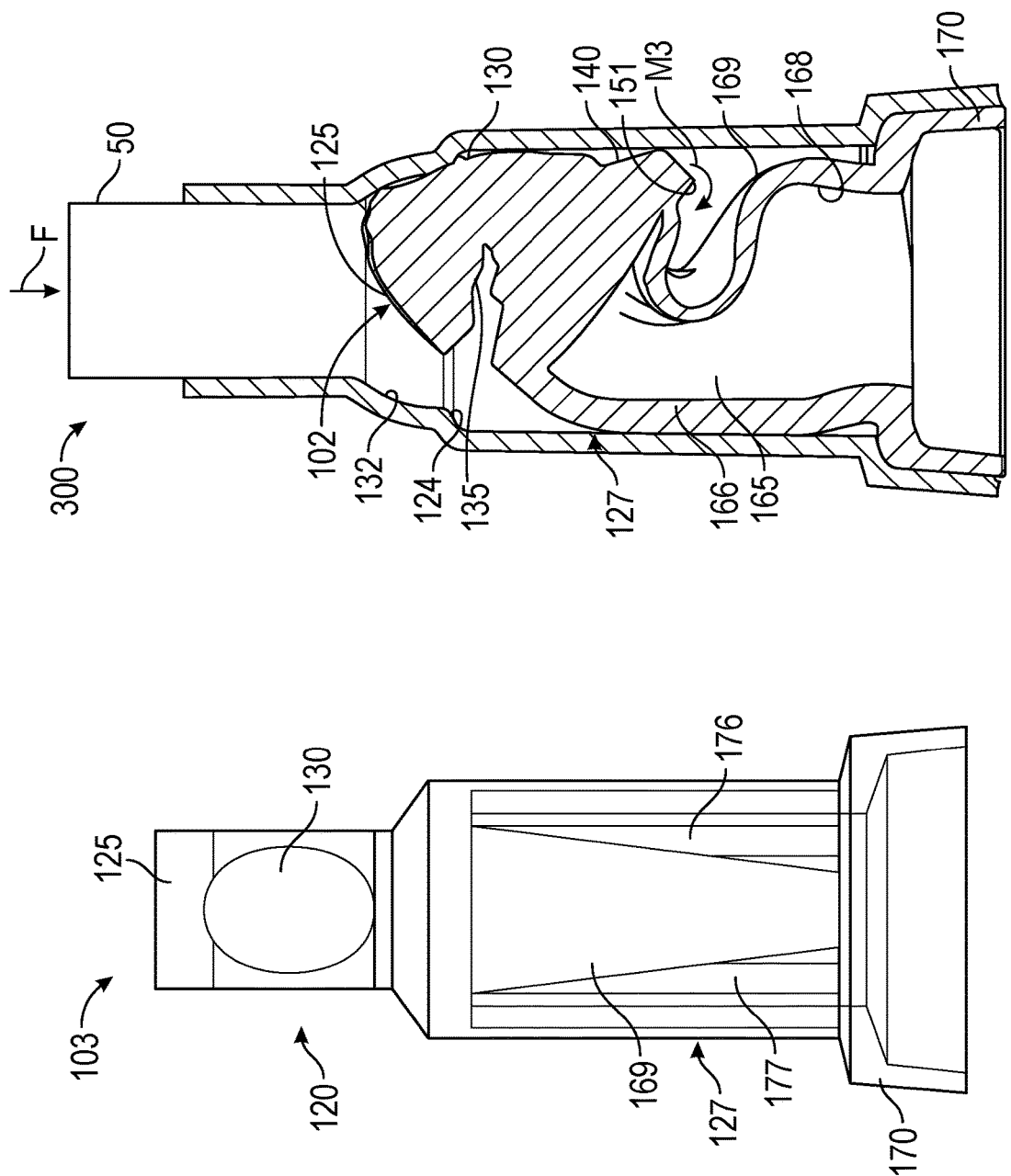

NEEDLELESS CONNECTOR WITH COMPRESSIBLE AND DEFLECTABLE VALVE

TECHNICAL FIELD

The present disclosure relates generally to needleless connectors, and, in particular, to needleless connectors with a valve member having a structure that when subject to an axial force may be capable of forcing one side of the valve body to buckle uniformly inward to minimize folding overlaps of the bucked valve wall.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Certain needleless connectors may be used in an IV set and may have a self-sealing port to prevent leakage of fluid when a mating medical implement is decoupled from such a needleless connector. Additionally, a needleless connector may include a mechanical valve, for example, a collapsible valve comprising a flexible material for providing the self-sealing port and controlling the flow of fluid within the IV set.

Due to the nature of many needleless valve geometries, fluid is commonly deposited on the face of the valve head upon removal of a medical implement (e.g., a mating male luer) used to apply an axial force to place the valve member in an open position. In these needless valves, fluid deposited on the valve head will occasionally separate from the valve member and flow into the fluid path for administering to a patient, thereby causing anxiety along with potential blood stream diseases.

The description provided in the background section should not be assumed to be prior art merely because it is mentioned in or associated with the background section. The background section may include information that describes one or more aspects of the subject technology.

SUMMARY

In accordance with various embodiments of the present disclosure, a needleless connector may include a housing having a proximal end defining an inlet port of the housing, a distal end configured to be coupled with a base of the housing, and an inner surface defining an internal cavity extending between the proximal end and the distal end, and a compressible valve disposed within the internal cavity. The compressible valve may include a head portion, a flange portion for securing the compressible valve in the housing, and a body portion extending between the head portion and the flange portion. The body portion may include a cylindrical outer surface including an external notch extending along a portion of a circumference of the cylindrical outer surface and recessed radially-inward from the cylindrical outer surface, and a planar face extending distally from the external notch and disposed between the external notch and the flange portion, The planar face may be recessed radially inward relative to at least a portion of the cylindrical outer surface.

In accordance with various embodiments of the present disclosure, a needleless connector may include a housing having a proximal end defining an inlet port of the housing, a distal end configured to be coupled with a base of the housing, and an inner surface defining an internal cavity extending between the proximal end and the distal end. The needleless connector may further include a compressible valve reciprocally disposed within the internal cavity. The compressible valve may include a head portion and a body portion extending distally from the head portion. The body portion may have a cylindrical outer surface including a cutout extending longitudinally along the cylindrical outer surface and recessed radially-inward from the cylindrical outer surface. The cutout may include a ramp surface.

In accordance with various embodiments of the present disclosure, a needleless connector may include a housing having a proximal end defining an inlet port of the housing, a distal end configured to be coupled with a base of the housing, and an inner surface defining an internal cavity extending between the proximal end and the distal end. The needleless connector may further include a compressible valve reciprocally disposed within the internal cavity. The compressible valve may include a head portion, and a body portion extending distally from the head portion. The body portion may include a cylindrical outer surface including an external notch extending along a portion of a circumference of the cylindrical outer surface and recessed radially-inward from the cylindrical outer surface. The needleless connector may include a collapsible segment disposed along at least a portion of the circumference of the cylindrical outer surface and recessed radially-inward from the cylindrical outer surface. The collapsible segment may be disposed distally to the external notch.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology.

BRIEF DESCRIPTION OF THE DRAWINGS

The following figures are included to illustrate certain aspects of the embodiments and should not be viewed as exclusive embodiments. The subject matter disclosed is capable of considerable modifications, alterations, combinations, and equivalents in form and function, as will occur to those skilled in the art and having the benefit of this disclosure.

FIG. 2A illustrates a cross-sectional view of a needleless connector including compressible valve, in accordance with some embodiments of the present disclosure.

FIG. 2B is a perspective view illustrating an example of the compressible valve of FIG. 2A, in accordance with some embodiments of the present disclosure.

FIG. 2C illustrates a cross-sectional view of a needleless connector including the compressible valve of FIG. 2B subject to an axial force, in accordance with some embodiments of the present disclosure.

FIG. 3A illustrates a cross-sectional view of a needleless connector including compressible valve, in accordance with some embodiments of the present disclosure.

FIG. 3B illustrates a cross-sectional view of a needleless connector including the compressible valve of FIG. 3A subject to an axial force, in accordance with some embodiments of the present disclosure.

FIGS. 4B, 4C, 4D, and 4E illustrate examples of the compressible valve of FIG. 4A, in accordance with some embodiments of the present disclosure.

FIG. 4F illustrates a cross-sectional view of a needleless connector including the compressible valve of FIGS. 4B-4E subject to an axial force, in accordance with some embodiments of the present disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular, but non-limiting, examples. Various embodiments described in the present disclosure may be carried out in different ways and variations, and in accordance with a desired application or implementation.

Figure 1B:
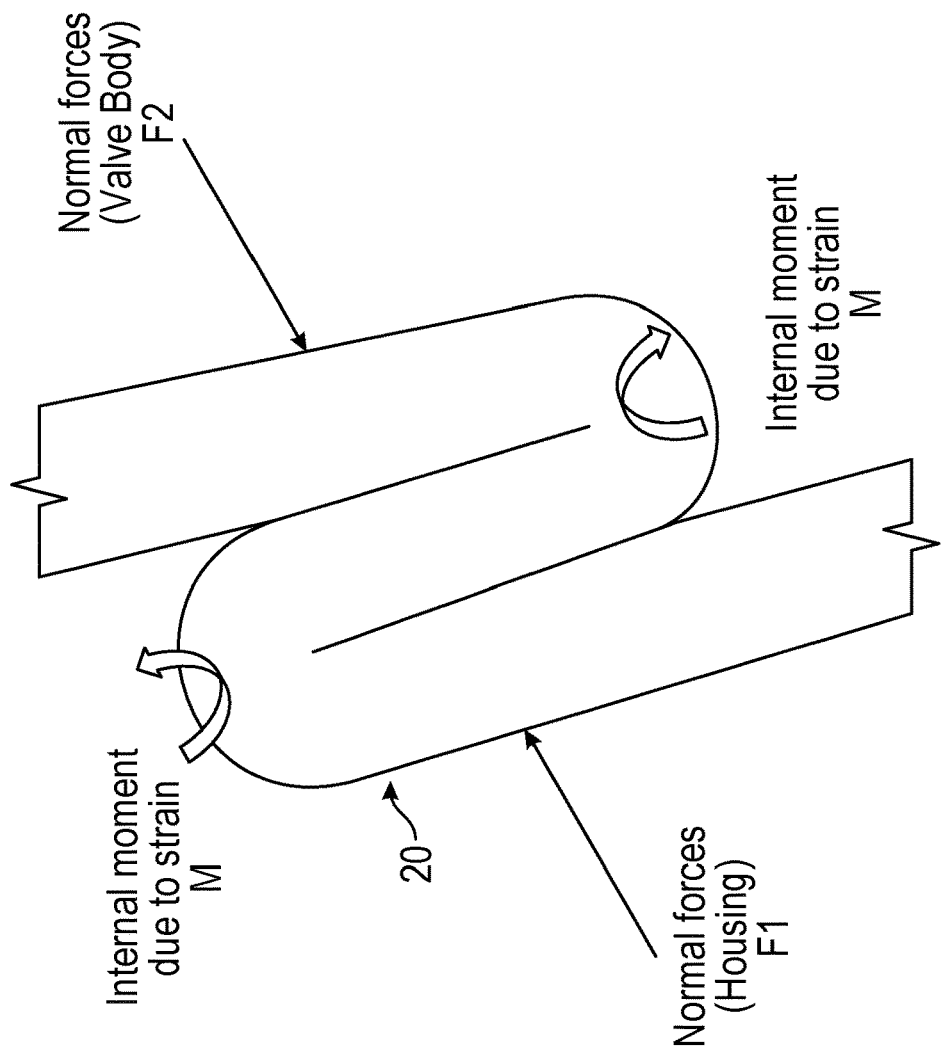
FIG. 1B is a sectional view of folding of the compressible valve of FIG. 1 along line 1B-1B.
Figure 1A:
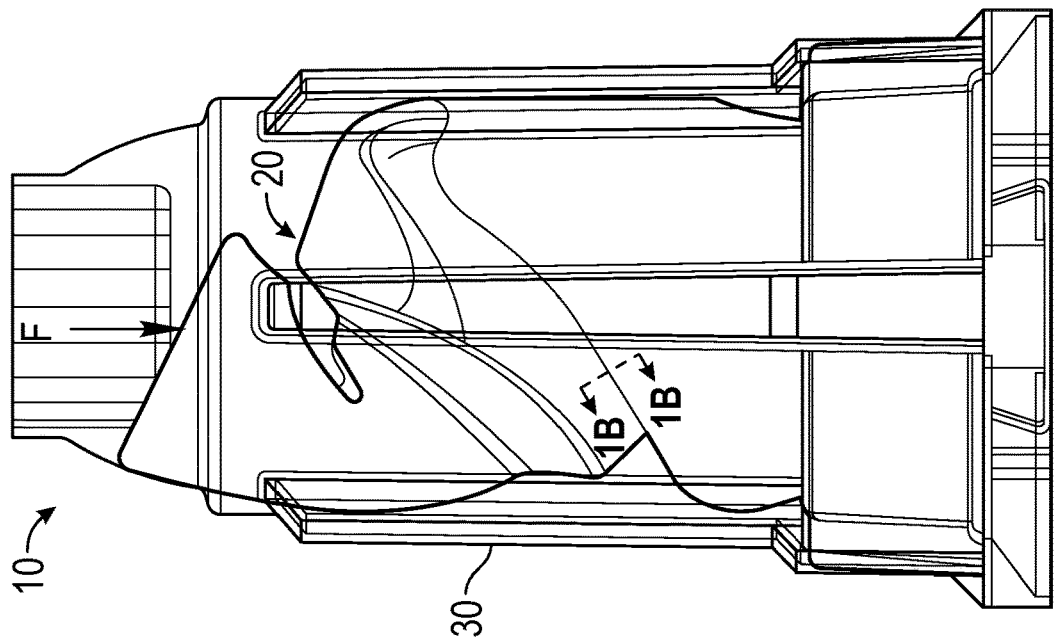
FIG. 1A is a perspective view of a needleless connector including compressible valve.

FIG. 1A is a perspective view of a needleless connector including compressible valve. FIG. 1B is a sectional view of folding of the compressible valve of FIG. 1 along line 1B-1B. As depicted, the needleless connector 10 may include a housing 30 and a compressible valve 20 disposed in an internal cavity of the housing 30. When an axial force F is exerted onto the compressible valve 20, the compressible valve deflects into a complex shape with significant overlapping of the deformed walls of the compressible valve. When the axial force F is removed, this overlapping of the deformed walls of the compressible valve 20 may disadvantageously contribute to a non-uniform return or expansion of the compressible valve 20 as the rebounding, returning, or expanding compressible valve 20 must first unfold in certain sections (e.g., as illustrated in FIG. 1B) before it can rebound, return, or expand back into its original position prior to application of the axial force F.

Finite element analysis of the deflected valve geometry shows that the buckled body portion of the compressible valve 20 folds onto itself causing significant overlap of the valve walls. The overlap of the valve walls may create a pinch point where normal forces F1 and F2 develop that act against an internal moment M caused by strain in the walls of the compressible valve 20 due to the deflected column of the compressible valve 20. The normal forces, in acting against the internal moment M, may disadvantageously prevent the walls of the compressible valve from freely expanding back to the uncompressed state of the compressible valve prior to application of the axial force F. In order to return to the uncompressed state after removal of the axial force, the compressible valve 20 must first act to unfold itself by pushing the valve walls inward to open space, before the internal moments M can spring the column of the compressible valve 20 back to its original shape. This causes the compressible valve 20 to take a longer time to expand or otherwise return to its uncompressed state once the axial force F is removed.

Accordingly, what is needed is a compressible valve design with a structure that when subject to an axial force may be capable of forcing one side of the valve body to buckle uniformly inward to minimize folding overlaps or overfolding of the bucked valve wall, thereby maximizing response or rebound time of the compressible valve.

Various embodiments of the present disclosure advantageously provide compressible valves having improved structures over the currently existing needleless valves which allow the valve wall to buckle or otherwise deflect when subject to an axial (compressing) force in such a way so as to achieve: 1) valve opening at a desired point, 2) a more even fluid displacement throughout insertion and removal of the axial force, and 3) a deflected shape of the compressible valve without significant overlapping of the valve wall so as to make the response speed more uniform when the axial force is removed.

While the following description is directed to the administration of medical fluid to a patient by a medical practitioner using the disclosed needleless connector, it is to be understood that this description is only an example of usage and does not limit the scope of the claims.

FIG. 2A illustrates a cross-sectional view of a needleless connector including compressible valve, in accordance with some embodiments of the present disclosure. FIG. 2C illustrates a cross-sectional view of a needleless connector including the compressible valve of FIG. 2B subject to an axial force, in accordance with some embodiments of the present disclosure.

Referring to FIG. 2A, the needleless connector 100 may include a housing 110 and a compressible valve 101 disposed in the housing 110. As depicted, the housing 110 may have a proximal end 103 defining an inlet port 105 of the housing 110, and a distal end 107 configured to be coupled with a base of the housing 110. In some embodiments, the housing 110 may further include an inner surface 132 defining an internal cavity 115 which extends at least partially between the proximal and distal ends 103 and 107. In some embodiments, the housing 110 may be in the form of an elongate cylindrical body having a central longitudinal axis $X_1$. However, in some embodiments, the housing may be formed from a combination of other pieces or parts similarly dimensioned to house the compressible valve 101 therein. In operation, a fluid pathway may be established through needleless connector 100 from the inlet port 105 into the internal cavity 115 and through an outlet port of the housing 110, for example. As referred to herein, proximal refers to an orientation toward the inlet port 105 of the housing 110, and distal refers to an orientation toward the bottom or distal end 107 of the housing 110, opposite the inlet port 105.

As depicted, the housing 100 may include the inlet port 105 for interfacing with a medical implement 50 (e.g., a male luer, a syringe, or other similar medical implement). In some embodiments, the distal end 107 of the housing 110 may have an increased diameter as compared with the proximal end 103 and include one or more internal contact tabs. When assembled in a needleless connector, the one or more internal contact tabs may provide a radial force substantially orthogonal to the central longitudinal axis $X_1$ onto a flange portion 170 of the compressible valve 101 that is arranged on a valve mount of the housing 110.

The inner surface 132 and the internal cavity 115 defined therein may extend longitudinally from a top surface of the opening of the inlet port 105 into the housing 110. In some embodiments, an internal sealing edge 124 may be defined on the inner surface 132 of the housing 110. The internal sealing edge 124 may be a circumferential edge and configured for retaining the compressible valve 101 within the internal cavity 115 of the assembled needleless connector 100. In operation, the internal sealing edge 124 may be arranged to provide blocking of fluid flow in conjunction with a primary seal portion 140 of the compressible valve 101.

FIG. 2B is a perspective view illustrating an example of the compressible valve 101 of FIG. 2A, in accordance with some embodiments of the present disclosure. FIG. 2B illustrates in isolation an example compressible valve 101. Compressible valve 101 may include head portion 120, and flange portion 170 for securing the compressible valve 101 in the housing 110. The compressible valve 101 may further include a body portion 122 extending distally from the head portion 120 between the head portion 120 and the flange portion 170.

In certain embodiments, the head portion 120 includes a column section 128 and may define a longitudinal central axis $X_2$ of the compressible valve 200 in a non-activated state (before an applied axial force F causes the head portion 120 to tilt, as illustrated in FIG. 2C). The longitudinal central axis $X_2$ may substantially correspond to the central longitudinal axis $X_1$ of the housing 110 when assembled therein in a closed state of the compressible valve 101. In the non-activated state (e.g., in isolation or within the housing 110 but not displaced by medical implement 50) the longitudinal central axis $X_2$ may extend longitudinally through the head portion 120 and the body portion 122 of the compressible valve 101 (as depicted in FIG. 2B). In the aforementioned state, the body portion 122 of the compressible valve 101 may have the same axial center as the head portion 120 or other portions of the compressible valve 101. However, as described in further detail below, in an activated state (e.g., when the axial force F is applied to the compressible valve 101 using the medical implement or syringe 50) the longitudinal central axis $X_2$ of the compressible valve 101 may change and pivot in relation to the central longitudinal axis $X_1$ upon the compressible valve 101 being activated by the medical implement or syringe 50.

In accordance with some embodiments, the head portion 120 of the compressible valve 101 may have a top section 129 that includes a top surface 125. The top section 129 may be in the form of a circumferential lip or similar protrusion for slidably and sealably engaging with the inlet port 105 of the needleless connector housing 110. In the assembled configuration of the compressible valve 101 and the housing 110, the top surface 125 may be oriented at a perpendicular plane angle with respect to the central longitudinal axis $X_1$ as illustrated in FIG. 2A. In some embodiments, the head portion 120 may include at least one notch disposed along the exterior thereof, adjacent to, and disposed distally to the top section 129. For example, as depicted, the head portion 120 may include a first notch 130 and a second notch 135 disposed on opposing sides of the exterior of the column section 128 of head portion 120.

In some embodiments, the first and second notches 130 and 135 may have a same or similar shape. For example, in some embodiments, the first and second notches 130 and 135 may be configured as arcuate-shaped recesses within the column section 128, and in other embodiments, the first and second notches 130 and 135 may be configured as v-shaped or conically-shaped recesses within the column section 128. In some embodiments, the first and second notches 130 and 135 may have different shapes. For example, in some embodiments, the first notch 130 may be configured as an arcuate-shaped recess within the column section 128, and the second notch 135 may be configured as a v-shaped or conically-shaped recess within the column section 128. In the illustrated embodiments, the first and second notches have different shapes. However, it is to be appreciated that the implementations of the first and second notches 30 and 135 may comprise a variety of shapes and sizes, such as, but not limited to, notches having arcuate, triangular, polygonal, or various geometric cross-section shapes, for example.

In some embodiments however, the column section 128 may not include notches, but may instead have discontinuity segments disposed thereon that operate in a similar manner as the first and second notches 130 and 135. For example, one side or a portion of each side of the head portion 120 may be formed of a different material (or a same material with a different hardness value) than the remainder of the head portion 120.

In accordance with various embodiments of the present disclosure, the top section 125 of the head portion 120 may define a first or secondary seal portion 129 of the compressible valve 101. The body portion 122 may further define a second or primary seal portion 140 at a proximal end of the body portion 122. As depicted, the primary seal portion 140 may be disposed distally to the secondary seal portion 129.

In some embodiments, as illustrated in FIGS. 2A and 2C, the body portion 122 may include a cylindrical outer surface 164, an internal surface 168 that defines a valve cavity 165, and a wall 166 defined between the internal surface 168 and the outer surface 164. In some embodiments, the cylindrical outer surface 164 may include an external notch 150 extending along a portion of a circumference of the cylindrical outer surface 164. In particular, as depicted, the external notch 150 may be recessed radially-inward from the cylindrical outer surface 164 into the wall 166. For example, in some embodiments, the external notch 150 may include a first surface 152 extending radially-inward from the outer circumferential surface 164, a second surface 154 extending longitudinally and distally from the first surface 152. As depicted, the external notch 150 may further include a ramp surface 156 extending distally and radially outward from the second surface 154. In some embodiments, a radial distance D1 between a distal end of the ramp surface 156 and the longitudinal central axis $X_2$ of the compressible valve 101 may be less than a radial distance D2 between a radially outward-most end of the first surface 152 and the longitudinal central axis $X_2$ of the compressible valve 101.

In accordance with various embodiments of the present disclosure, the compressible valve 101 may further include a planar face 160 extending distally from the external notch 150 and disposed between the external notch 150 and the flange portion 170. In particular, the planar face 160 may be a flat surface which extends from a distal end of the ramp surface 156 to a proximal end of the flange portion 170. Accordingly, as illustrated, the planar face 160 may be recessed radially-inward relative to the outer circumferential surface 164.

In some embodiments, the compressible valve 101 may further include an internal notch 158 disposed on the internal surface 168 of body portion 122 and extending radially outward into the wall 166 towards the planar face 160. As depicted, a longitudinal position of the internal notch 158 along a length of the wall 166 may overlap at least in part with a longitudinal position of the external notch 150 along the length of the wall.

The aforementioned configuration and structure of the compressible valve 101 with valve wall having internal and external notches and an inwardly-recessed planar face is advantageous in that when subject to a threshold axial force, one side of the compressible valve may buckle uniformly inward (as illustrated in FIG. 2C) to minimize folding overlaps or overfolding of the buckled valve wall 166, thereby maximizing response or rebound time of the compressible valve. In particular, in operation, when the axial force F is applied to the compressible valve 101, the compressible valve 101 may be compressed and buckle uniformly inward from a sealed configuration of the needleless connector 100 (illustrated in FIG. 2A) to an unsealed (open) configuration illustrated in FIG. 2C as described below.

In operation, as the medical implement 50 (e.g., a male luer, a syringe, or any similar medical implement) is initially inserted into the inlet port 105 of the needleless connector 100, an axial force F is exerted onto the compressible valve 101 such that the second notch 135 may fold or collapse and the first notch 130 may open or expand such that the top section 129 may tilt downwardly. In this regard, a fluid path from the medical implement 50 in the inlet port 105 may be established through the internal cavity 115 of the housing 110 to an outlet port of the housing 110. In some embodiments, the axial force F is exerted onto the compressible valve 101 such that the valve wall 166 at the exterior notch 150 may slightly bow inward towards the valve cavity 165, and the valve wall 166 at the interior notch 158 may slightly bow outwards towards valve cavity 165. Additionally, the primary seal portion 140 may separate from the internal sealing edge 124.

As the medical implement 50 continues to exert axial force F onto the compressible valve 101, the medical implement 50 descends further into the inlet port 105, and due to the bowing of the external and internal notches 150 and 158 and the inwardly-recessed structure of the planar face 160, as the compressible valve 101 is further compressed, a moment M1 is created about a proximal end of the planar face 160 thereby causing the body portion 122 to buckle uniformly inward as illustrated in FIG. 2C. Since the body portion 122 buckles uniformly inward at the planar face 160, overfolding and/or folding overlaps of the valve wall 166 are prevented from occurring. The aforementioned configuration is advantageous over the currently existing valves of needless connectors, e.g., as illustrated in FIG. 1A in that since folding overlaps of the valve wall 166 are prevented from occurring, the problematic pinch points—where normal forces traditionally develop which act against an internal moment caused by strain in the valve wall due to the deflected column and prevent the valve wall from freely opening during return—do not occur in the compressible valve 101 of the various embodiments described herein. Advantageously, since the compressible valve 101 has minimal folding, upon removal of the axial force F, the valve wall 166 may freely expand and more quickly return to the uncompressed state illustrated in FIG. 2A as compared with the currently existing compressible valve 20 of FIG. 1A.

FIG. 3A illustrates a cross-sectional view of a needleless connector 200 including compressible valve 102, in accordance with some embodiments of the present disclosure. FIG. 3B illustrates a cross-sectional view of a needleless connector including the compressible valve 102 of FIG. 3A subject to an axial force F, in accordance with some embodiments of the present disclosure. In some embodiments, the compressible valve 102 of needleless connector 200 may have similar features and be similar in structure and function to the compressible valve 101 of needleless connector with a slight variation in the structure of the external notch 153 and the planar face 161. For example, referring to FIG. 3A, the needleless connector 200 may include the housing 110 and a compressible valve 102 disposed in the housing 110. The housing 110 has been described in detail above with respect to the needleless connector 100 of FIGS. 2A and 2C, therefore a detailed description thereof shall be omitted with respect to the needleless connector 200.

In some embodiments, an internal sealing edge 124 may be defined on the inner surface 132 of the housing 110. The internal sealing edge 124 may be a circumferential edge and configured for retaining the compressible valve 102 within the internal cavity 115 of the assembled needleless connector 200. In operation, the internal sealing edge 124 may be arranged to provide blocking of fluid flow in conjunction with a primary seal portion 140 of the compressible valve 102.

According to various embodiments of the present disclosure, the compressible valve 102 may include head portion 120, and flange portion 170 for securing the compressible valve 102 in the housing 110. The compressible valve 102 may further include a body portion 123 extending distally from the head portion 120 between the head portion 120 and the flange portion 170.

The head portion 120 and the flange portion 170 have been described in detail above with respect to the needleless connector 100 of FIGS. 2A and 2C, therefore a detailed description thereof shall be omitted with respect to the needleless connector 200. According to various embodiments of the present disclosure, the compressible valve 102 may have a longitudinal central axis $X_3$. In the non-activated state (e.g., in isolation or within the housing 110 but not displaced by medical implement 50) the longitudinal central axis $X_3$ may extend longitudinally through the head portion 120 and the body portion 123 of the compressible valve 102. In the aforementioned state, the body portion 123 of the compressible valve 102 may have the same axial center as the head portion 120 or other portions of the compressible valve 102. However, as described in further detail below, in an activated state (e.g., when the axial force F is applied to the compressible valve 102 using the medical implement or syringe 50) the longitudinal central axis $X_3$ of the compressible valve 102 may change and pivot in relation to the central longitudinal axis $X_1$ upon the compressible valve 102 being activated by the medical implement or syringe 50.

In accordance with various embodiments of the present disclosure, the top section 125 of the head portion 120 may define a first or secondary seal portion 129 of the compressible valve 102. The body portion 123 may further define a second or primary seal portion 140 at a proximal end of the body portion 123. As depicted, the primary seal portion 140 may be disposed distally to the secondary seal portion 129.

In some embodiments, as illustrated in FIGS. 3A and 3B, the body portion 123 may include a cylindrical outer surface 164, an internal surface 168 that defines a valve cavity 165, and a wall 166 defined between the internal surface 168 and the outer surface 164. In some embodiments, the cylindrical outer surface 164 may include an external notch 153 extending along a portion of a circumference of the cylindrical outer surface 164. In particular, as depicted, similar to the external notch 150 of compressible valve 101, the external notch 153 may be recessed radially-inward from the cylindrical outer surface 164 into the wall 166. For example, in some embodiments, the external notch 150 may include a first surface 151 extending radially-inward from the outer circumferential surface 164, a second surface 155 extending longitudinally and distally from the first surface 152. As depicted, the external notch 150 may further include a ramp surface 157 extending distally and radially outward from the second surface 155. Similar to the compressible valve 101, a radial distance D1 between a distal end of the ramp surface 157 and the longitudinal central axis $X_3$ of the compressible valve 102 may be less than a radial distance D4 between a radially outward-most end of the first surface 151 and the longitudinal central axis $X_3$ of the compressible valve 102.

In accordance with various embodiments of the present disclosure, the compressible valve 102 may further include a planar face 161 extending distally from the external notch 153 and disposed between the external notch 153 and the flange portion 170. In particular, the planar face 161 may be a flat surface which extends from a distal end of the ramp surface 157 to a proximal end of the flange portion 170. Accordingly, as illustrated, the planar face 161 may be recessed radially-inward relative to the outer circumferential surface 164. The compressible valve 102 may be substantially similar to the compressible valve 101, with a difference being that the planar face 160 is recessed further radially-inward from the outer circumferential surface 164 than the planar face 161 is recessed from the outer circumferential surface 164.

In some embodiments, the compressible valve 102 may further include an internal notch 158 disposed on the internal surface 168 of body portion 123 and extending radially outward into the wall 166 towards the planar face 161. As depicted, a longitudinal position of the internal notch 158 along a length of the wall 166 may overlap at least in part with a longitudinal position of the external notch 153 along the length of the wall 166.

The aforementioned configuration and structure of the compressible valve 102 with valve wall having internal and external notches 158 and 153, and an inwardly-recessed planar face 161 is advantageous in that when subject to an axial force, one side of the compressible valve 102 may buckle uniformly inward (as illustrated in FIG. 3B) to minimize folding overlaps or overfolding of the buckled valve wall 166, thereby maximizing response or rebound time of the compressible valve. In particular, in operation, when the axial force F is applied to the compressible valve 102, the compressible valve 102 may be compressed and buckle uniformly inward from a sealed configuration of the needleless connector 200 (illustrated in FIG. 3A) to an unsealed (open) configuration illustrated in FIG. 3B as described below.

In operation, as the medical implement 50 (e.g., a male luer, a syringe, or any similar medical implement) is initially inserted into the inlet port 105 of the needleless connector 200, an axial force F is exerted onto the compressible valve 102 such that the second notch 135 may fold or collapse and the first notch 130 may open or expand such that the top section 129 may tilt downwardly. In this regard, a fluid path from the medical implement 50 in the inlet port 105 may be established through the internal cavity 115 of the housing 110 to an outlet port of the housing 110. In some embodiments, the axial force F is exerted onto the compressible valve 102 such that the valve wall 166 at the exterior notch 153 may slightly bow inward towards the valve cavity 165, and the valve wall 166 at the interior notch 158 may slightly bow outwards towards valve cavity 165. Additionally, the primary seal portion 140 may separate from the internal sealing edge 124.

As the medical implement 50 continues to exert axial force F onto the compressible valve 102, the medical implement 50 descends further into the inlet port 105, and due to the bowing of the external and internal notches 153 and 158 and the inwardly-recessed structure of the planar face 161, as the compressible valve 102 is further compressed, a moment M2 is created about a proximal end of the planar face 161 thereby causing the body portion 123 to buckle uniformly inward as illustrated in FIG. 3B. Since the body portion 123 buckles uniformly inward at the planar face 161, overfolding and/or folding overlaps of the valve wall 166 are prevented from occurring. The aforementioned configuration is advantageous over the currently existing valves of needless connectors, for example, as illustrated in FIG. 1A in that since folding overlaps of the valve wall 166 are prevented from occurring, the problematic pinch points—where normal forces traditionally develop which act against an internal moment caused by strain in the valve wall due to the deflected column and prevent the valve wall from freely opening during return—do not occur in the compressible valve 102. Advantageously, since the compressible valve 102 has minimal folding, upon removal of the axial force F, the valve wall 166 may freely expand and more quickly return to the uncompressed state illustrated in FIG. 3A as compared with the currently existing compressible valve 20 of FIG. 1A.

Figure 4B:
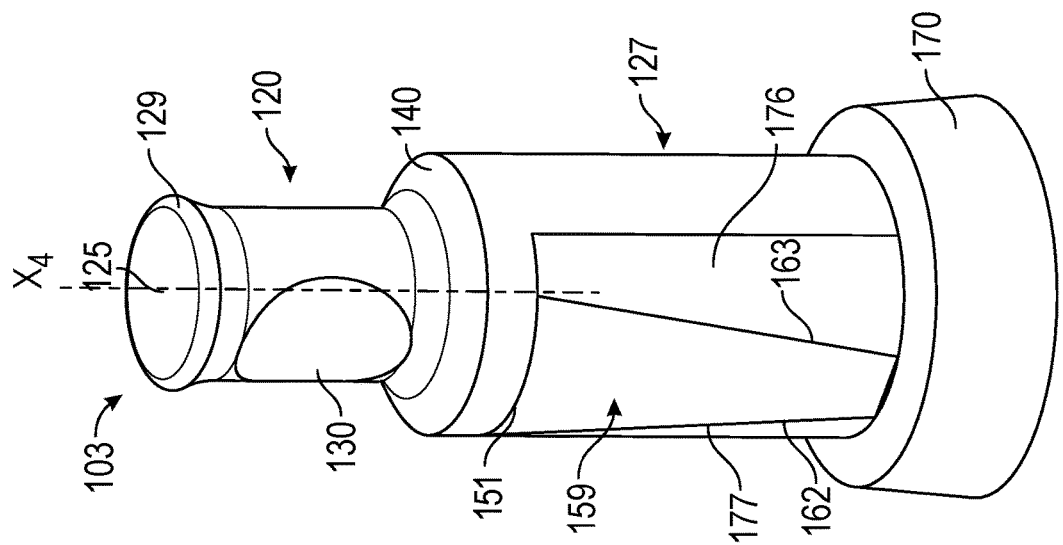
Figure 4A:
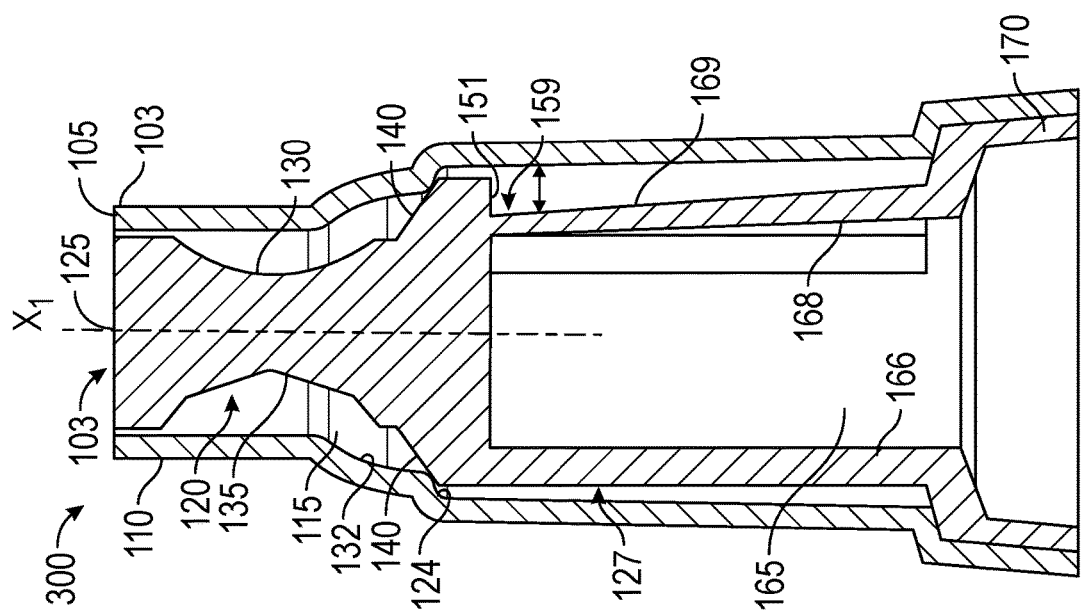
FIG. 4A illustrates a cross-sectional view of a needleless connector including compressible valve, in accordance with some embodiments of the present disclosure.

FIG. 4A illustrates a cross-sectional view of a needleless connector 300 including compressible valve 103, in accordance with some embodiments of the present disclosure. FIGS. 4B, 4C, 4D, and 4E illustrate an example of the compressible valve 103 of FIG. 4A, in accordance with some embodiments of the present disclosure. FIG. 4F illustrates a cross-sectional view of the needleless connector 300 including the compressible valve 103 of FIGS. 4B-4E subject to an axial force F, in accordance with some embodiments of the present disclosure.

Referring to FIG. 4A, the needleless connector 300 may include a housing 110 and a compressible valve 103 disposed in the housing 110. The housing 110 has been described in detail above with respect to the needleless connector 100 of FIGS. 2A and 2C, therefore a detailed description thereof shall be omitted with respect to the needleless connector 300.

In some embodiments, an internal sealing edge 124 may be defined on the inner surface 132 of the housing 110. The internal sealing edge 124 may be a circumferential edge and configured for retaining the compressible valve 103 within the internal cavity 115 of the assembled needleless connector 300. In operation, the internal sealing edge 124 may be arranged to provide blocking of fluid flow in conjunction with a primary seal portion 140 of the compressible valve 103.

According to various embodiments of the present disclosure, the compressible valve 103 may include head portion 120, and flange portion 170 for securing the compressible valve 103 in the housing 110. The compressible valve 103 may further include a body portion 127 extending distally from the head portion 120 between the head portion 120 and the flange portion 170.

The head portion 120 and the flange portion 170 have been described in detail above with respect to the needleless connector 100 of FIGS. 2A and 2C, therefore a detailed description thereof shall be omitted with respect to the needleless connector 300. According to various embodiments of the present disclosure, the compressible valve 103 may have a longitudinal central axis $X_4$. In the non-activated state (e.g., in isolation or within the housing 110 but not displaced by medical implement 50) the longitudinal central axis $X_4$ may extend longitudinally through the head portion 120 and the body portion 127 of the compressible valve 103. In the aforementioned state, the body portion 127 of the compressible valve 102 may have the same axial center as the head portion 120 or other portions of the compressible valve 103. However, as described in further detail below, in an activated state (e.g., when the axial force F is applied to the compressible valve 103 using the medical implement or syringe 50) the longitudinal central axis $X_4$ of the compressible valve 103 may change and pivot in relation to the central longitudinal axis $X_1$ upon the compressible valve 103 being activated by the medical implement or syringe 50.

In accordance with various embodiments of the present disclosure, the top section 125 of the head portion 120 may define a first or secondary seal portion 129 of the compressible valve 102. The body portion 127 may further define a second or primary seal portion 140 at a proximal end of the body portion 127. As depicted, the primary seal portion 140 may be disposed distally to the secondary seal portion 129.

In some embodiments, as illustrated in FIGS. 4B-4E, the body portion 127 may include a cylindrical outer surface 164, an internal surface 168 that defines a valve cavity 165, and a wall 166 defined between the internal surface 168 and the outer surface 164. In some embodiments, the cylindrical outer surface 164 may include a cutout 159 extending longitudinally along the cylindrical outer surface 164. In particular, the cutout 159 may include a first surface 151 recessed radially-inward from the cylindrical outer surface 164, and a ramp surface 169 extending distally and radially outward from the first surface 151. For example, in some embodiments, the ramp surface 169 may extend from a radially inward-most end of the first surface 151. Accordingly, a proximal end of the ramp surface 169 may be disposed further radially-inward than a distal end of the ramp surface 169.

In accordance with various embodiments of the present disclosure, the ramp surface 169 may be a planar surface extending distally from the radially inward-most end of the first surface 151 and disposed between the first surface 151 and the flange portion 170. In particular, the ramp surface 151 may be a flat surface which extends from the radially inward-most end of the first surface 151 to a proximal end of the flange portion 170. Accordingly, as illustrated, a proximal end of the ramp surface 169 may be recessed radially-inward relative to the outer circumferential surface 164.

In some embodiments, the cutout 159 may be a wedge-shaped or conically-shaped cutout. For example, as illustrated in FIGS. 4B and 4E, the ramp surface 169 may include first and second opposing sides 162 and 163 which may be angled outwardly away from each other at the first surface 151, and angled inwardly towards each other at the proximal end of the flange portion 170.

According to various embodiments of the present disclosure, the compressible valve 103 may further include secondary cutouts 176 and 177 extending longitudinally along the cylindrical outer surface 164 and recessed radially-inward from the cylindrical outer surface 164. As depicted, the secondary cutouts 176 and 177 may be disposed on opposing sides of the ramp surface 169 of the cutout 159.

The aforementioned configuration and structure of the compressible valve 102 with valve wall having the inwardly-recessed cutout 159 with planar ramp surface 169 is advantageous in that when subject to an axial force, one side of the compressible valve 103 may buckle uniformly inward (as illustrated in FIG. 4F) to minimize folding overlaps or overfolding of the buckled valve wall 166, thereby maximizing response or rebound time of the compressible valve 103. In particular, in operation, when the axial force F is applied to the compressible valve 103, the compressible valve 103 may be compressed and buckle uniformly inward from a sealed configuration of the needleless connector 300 (illustrated in FIG. 4A) to an unsealed (open) configuration illustrated in FIG. 4F as described below.

In operation, as the medical implement 50 (e.g., a male luer, a syringe, or any similar medical implement) is initially inserted into the inlet port 105 of the needleless connector 300, an axial force F is exerted onto the compressible valve 102 such that the second notch 135 may fold or collapse and the first notch 130 may open or expand such that the top section 129 may tilt downwardly. In this regard, a fluid path from the medical implement 50 in the inlet port 105 may be established through the internal cavity 115 of the housing 110 to an outlet port of the housing 110. In some embodiments, the axial force F is exerted onto the compressible valve 103 such that the valve wall 166 at the cutout 159 may slightly bow inward towards the valve cavity 165. Additionally, the primary seal portion 140 may separate from the internal sealing edge 124.

As the medical implement 50 continues to exert axial force F onto the compressible valve 103, the medical implement 50 descends further into the inlet port 105, and due to the bowing of the inwardly-recessed cutout 159 and the planar ramp surface 169, as the compressible valve 103 is further compressed, a moment M3 is created about a proximal end of the planar ramp surface 169 thereby causing the body portion 127 to buckle uniformly inward as illustrated in FIG. 4F. Since the body portion 127 buckles uniformly inward at the planar ramp surface 169, overfolding and/or folding overlaps of the valve wall 166 are prevented from occurring. The aforementioned configuration is advantageous over the currently existing valves of needless connectors, for example, as illustrated in FIG. 1A in that since folding overlaps of the valve wall 166 are prevented from occurring, the problematic pinch points—where normal forces traditionally develop which act against an internal moment caused by strain in the valve wall due to the deflected column and prevent the valve wall from freely opening during return—do not occur in the compressible valve 103. Advantageously, since the compressible valve 103 has minimal folding, upon removal of the axial force F, the valve wall 166 may freely expand and more quickly return to the uncompressed state illustrated in FIG. 4A as compared with the currently existing compressible valve 20 of FIG. 1A.

Figure 5B:
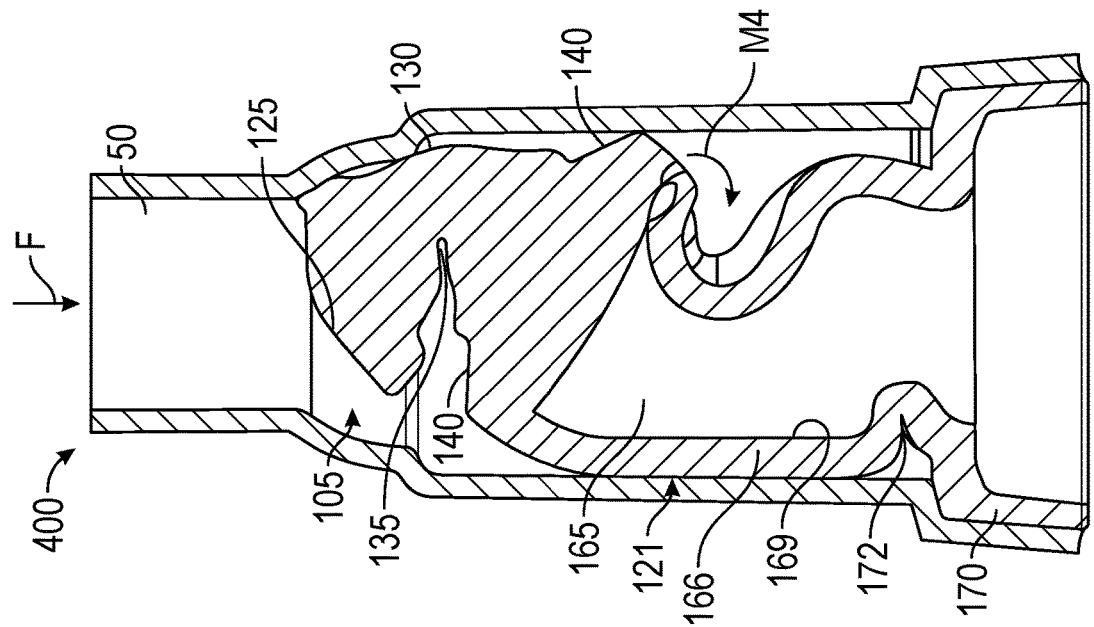
FIG. 5B illustrates a cross-sectional view of the needleless connector of FIG. 5A including the compressible valve subject to an axial force, in accordance with some embodiments of the present disclosure.
Figure 5A:
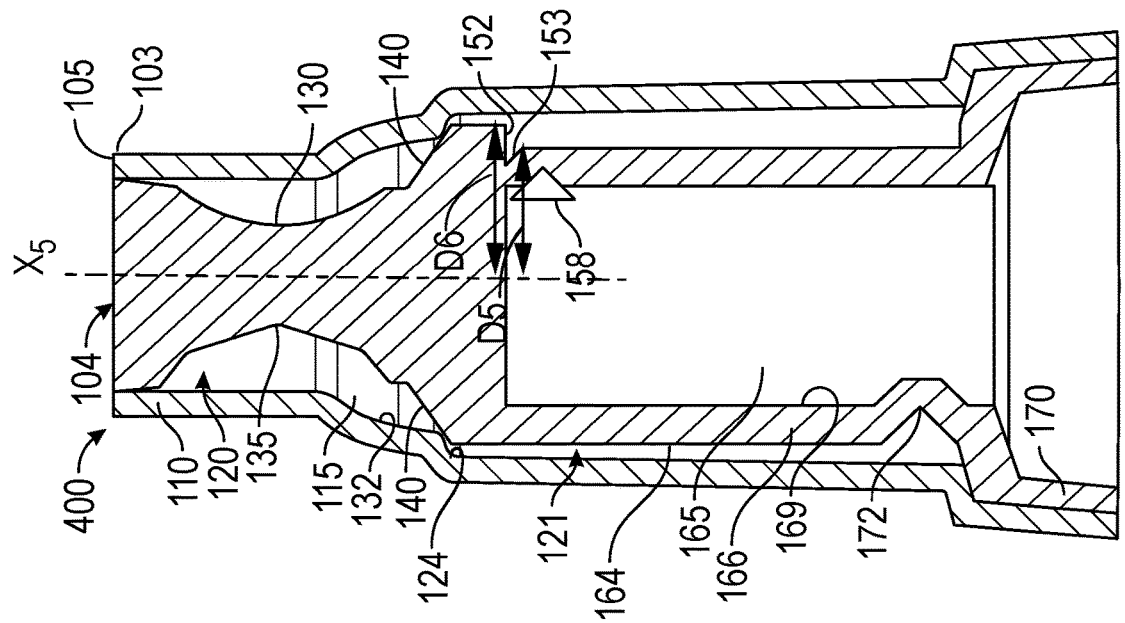
FIG. 5A illustrates a cross-sectional view of a needleless connector including compressible valve, in accordance with some embodiments of the present disclosure.

FIG. 5A illustrates a cross-sectional view of a needleless connector 400 including compressible valve 104, in accordance with some embodiments of the present disclosure. FIG. 5B illustrates a cross-sectional view of the needleless connector 400 of FIG. 5A including the compressible valve 104 subject to an axial force, in accordance with some embodiments of the present disclosure. Referring to FIG. 5A, the needleless connector 400 may include a housing 110 and the compressible valve 104 disposed in the housing 110. The housing 110 has been described in detail above with respect to the needleless connector 100 of FIGS. 2A and 2C, therefore a detailed description thereof shall be omitted with respect to the needleless connector 400.

In some embodiments, an internal sealing edge 124 may be defined on the inner surface 132 of the housing 110. The internal sealing edge 124 may be a circumferential edge and configured for retaining the compressible valve 104 within the internal cavity 115 of the assembled needleless connector 400. In operation, the internal sealing edge 124 may be arranged to provide blocking of fluid flow in conjunction with a primary seal portion 140 of the compressible valve 104.

According to various embodiments of the present disclosure, the compressible valve 104 may include head portion 120, and flange portion 170 for securing the compressible valve 104 in the housing 110. The compressible valve 104 may further include a body portion 121 extending distally from the head portion 120 between the head portion 120 and the flange portion 170.

The head portion 120 and the flange portion 170 have been described in detail above with respect to the needleless connector 100 of FIGS. 2A and 2C, therefore a detailed description thereof shall be omitted with respect to the needleless connector 400. According to various embodiments of the present disclosure, the compressible valve 104 may have a longitudinal central axis $X_5$. In the non-activated state (e.g., in isolation or within the housing 110 but not displaced by medical implement 50) the longitudinal central axis $X_5$ may extend longitudinally through the head portion 120 and the body portion 121 of the compressible valve 104. In the aforementioned state, the body portion 121 of the compressible valve 104 may have the same axial center as the head portion 120 or other portions of the compressible valve 104. However, as described in further detail below, in an activated state (e.g., when the axial force F is applied to the compressible valve 104 using the medical implement or syringe 50) the longitudinal central axis $X_5$ of the compressible valve 104 may change and pivot in relation to the central longitudinal axis $X_1$ of the housing 110 upon the compressible valve 104 being activated by the medical implement or syringe 50.

In accordance with various embodiments of the present disclosure, the top section 125 of the head portion 122 may define a first or secondary seal portion 129 of the compressible valve 104. The body portion 123 may further define a second or primary seal portion 140 at a proximal end of the body portion 123. As depicted, the primary seal portion 140 may be disposed distally to the secondary seal portion 129.

In some embodiments, as illustrated in FIGS. 5A and 5B, the body portion 121 may include a cylindrical outer surface 164, an internal surface 168 that defines a valve cavity 165, and a wall 166 defined between the internal surface 168 and the outer surface 164. In some embodiments, the cylindrical outer surface 164 may include a first external notch 142 extending along a portion of a circumference of the cylindrical outer surface 164. In particular, as depicted, the external notch 142 may be recessed radially-inward from the cylindrical outer surface 164 into the wall 166. For example, in some embodiments, the external notch 150 may include a first surface 143 extending radially-inward from the outer circumferential surface 164 and a ramp surface 144 extending distally and radially outward from the first surface 143. Similar to the compressible valve 101, a radial distance D5 between a distal end of the ramp surface 144 and the longitudinal central axis $X_5$ of the compressible valve 104 may be less than a radial distance D6 between a radially outward-most end of the first surface 143 and the longitudinal central axis $X_3$ of the compressible valve 102.

In accordance with various embodiments of the present disclosure, the compressible valve 104 may further include a planar face 171 extending distally from the external notch 142 and disposed between the external notch 142 and the flange portion 170. In particular, the planar face 171 may be a flat surface which extends from a distal end of the ramp surface 144 to a proximal end of the flange portion 170. Accordingly, as illustrated, the planar face 171 may be recessed radially-inward relative to the outer circumferential surface 164.

In some embodiments, the compressible valve 104 may further include an internal notch 158 disposed on the internal surface 168 of body portion 121 and extending radially outward into the wall 166 towards the planar face 171. As depicted, a longitudinal position of the internal notch 158 along a length of the wall 166 may overlap at least in part with a longitudinal position of the external notch 142 along the length of the wall 166.

Connectors (e.g., needleless connectors) that involve one or more moving parts can result in displacement of fluid volume within the connector. Displacement of fluid volume can be positive or negative. A change in the fluid volume in the needleless connector 104 can be determined as the difference in the change in volume above the primary seal portion 140 (as the axial force F is applied and the medical implement is inserted into the housing 110) and the change in the volume of the valve cavity 165 as the valve collapses. At any point during the insertion of the medical implement, the difference between the change in volume above the primary seal portion 140 and the change in the volume of the valve cavity 165 will determine if the fluid displaced is positive or negative.

Figure 7:
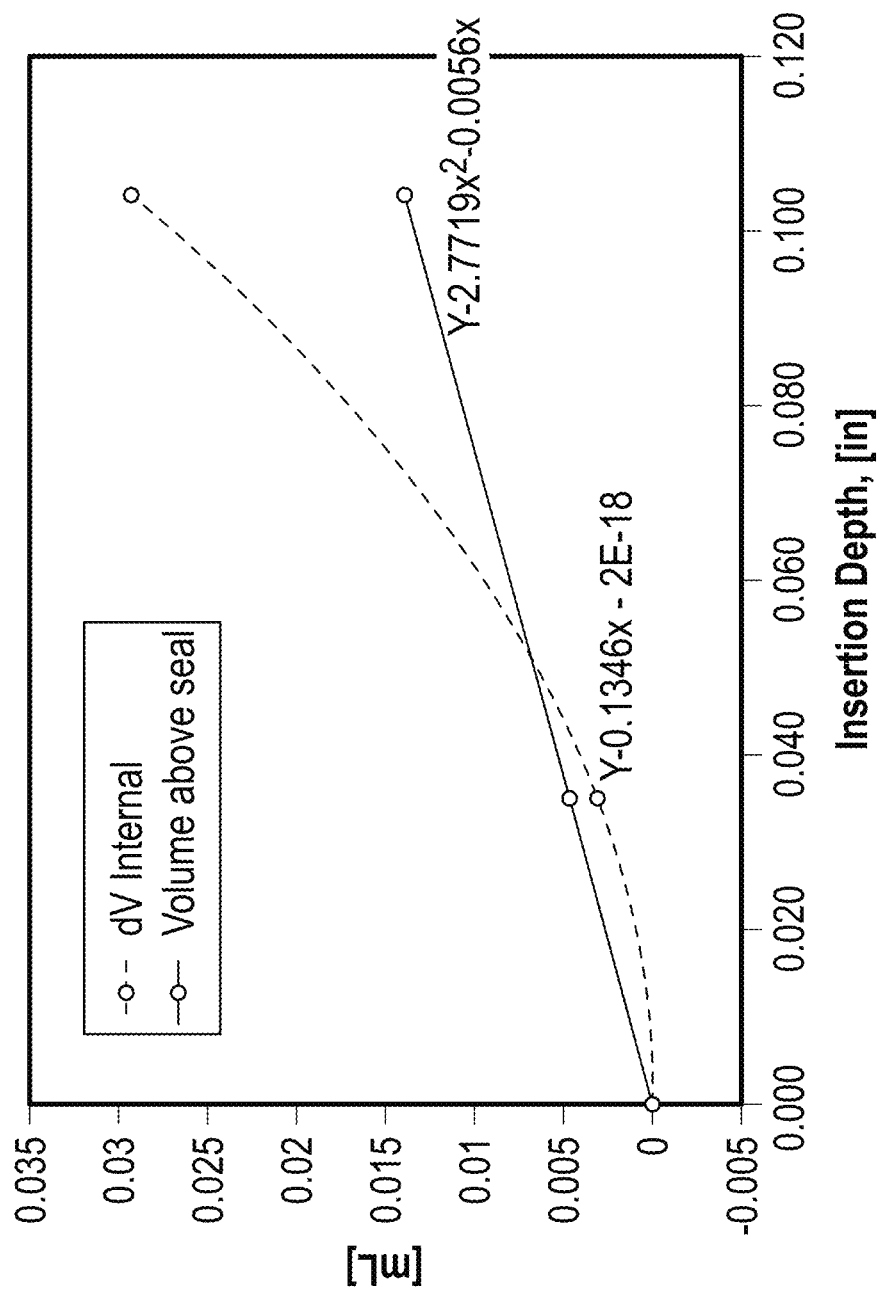
FIG. 7 is a graph illustrating a change in volume above the primary seal portion relative to a change in the volume of the valve cavity for in a needleless connector, in accordance with some embodiments of the present disclosure.

Table 1 above is an example illustration of how the change in volume above the primary seal portion 140 (Volume above seal) and the change in the volume of the valve cavity 165 (dV Internal) vary may over various insertion depths of the medical implement 50 in the needleless connectors without the collapsible segment 172. For example, as illustrated in Table 1 and in the graph of FIG. 7, for the first 0.050 inches of insertion depth, the difference between the change in volume above the primary seal portion 140 and the change in the volume of the valve cavity 165 is expected to yield a positive fluid displacement. As the medical implement is further inserted, past the 0.05 inches insertion depth, the valve chamber may then begin to buckle and compress as described above at a faster rate than the volume above the primary seal portion 140 increases. Accordingly, after the 0.05 inches insertion depth of the medical implement, the difference between the change in volume above the primary seal portion 140 and the change in the volume of the valve cavity 165 is expected to yield a negative fluid displacement.

The various embodiments of the present disclosure illustrated in FIGS. 5A and 5B are directed to advantageously providing a configuration in which the difference between the change in volume above the primary seal portion 140 and the change in the volume of the valve cavity 165 is expected to yield and maintain a uniform negative fluid displacement throughout insertion of the medical implement. Accordingly, the difference between the change in volume above the primary seal portion 140 and the change in the volume of the valve cavity 165 is expected to advantageously yield and maintain a uniform positive fluid displacement throughout removal of the medical implement as described in further detail below.

According to various embodiments of the present disclosure, as illustrated in FIGS. 5A and 5B, the body portion 121 of compressible valve 104 may further include a collapsible segment 172 extending along at least a portion of the circumference of the cylindrical outer surface 164. The collapsible segment 172 may be recessed radially-inward from the cylindrical outer surface 164. In some embodiments, the collapsible segment 172 may be disposed distally to the external notch 142. For example, as depicted, the collapsible segment 172 may be disposed at a distal and of the body portion 121 which may also correspond to the proximal end of the flange portion 170.

The collapsible segment 172 may be configured such that when an axial force F is applied to the head portion 120 of the compressible valve 104, the collapsible segment 172 collapses radially inward thereby causing downward (i.e., distal) displacement and/or vertical crushing/compressing of the compressible valve 104. Accordingly, due to the downward collapsing of the collapsible segment 172, the body portion 121 may first vertically crush/compress prior to buckling inward as illustrated in FIG. 5B. The configuration of the compressible valve 104 having the collapsible segment 172 on the body portion 121 is advantageous in achieving a more uniform negative displacement during initial insertion of the medical implement 50. This in turn allows for a more uniform positive volume displacement upon removal of the axial force F, thereby allowing the compressible valve to more quickly spring back and expand to the uncompressed state illustrated in FIG. 5A as compared with the currently existing compressible valve 20 of FIG. 1A.

Additionally, the aforementioned configuration and structure of the compressible valve 104 with valve wall having internal and external notches 158 and 142, and an inwardly-recessed planar face 161 is advantageous in that when subject to the axial force F, one side of the compressible valve 102 may buckle uniformly inward (as illustrated in FIG. 5B) to minimize folding overlaps or overfolding of the buckled valve wall 166, thereby maximizing response or rebound time of the compressible valve. In particular, in operation, when the axial force F is applied to the compressible valve 102, the compressible valve 104 may be compressed and buckle uniformly inward from a sealed configuration of the needleless connector 400 (illustrated in FIG. 4A) to an unsealed (open) configuration illustrated in FIG. 4B as described below.

In operation, as the medical implement 50 (e.g., a male luer, a syringe, or any similar medical implement) is initially inserted into the inlet port 105 of the needleless connector 400, an axial force F is exerted onto the compressible valve 104 such that the second notch 135 may fold or collapse and the first notch 130 may open or expand such that the top section 129 may tilt downwardly. In this regard, a fluid path from the medical implement 50 in the inlet port 105 may be established through the internal cavity 115 of the housing 110 to an outlet port of the housing 110. In some embodiments, the axial force F is exerted onto the compressible valve 104 such that the valve wall 166 at the exterior notch 142 may slightly bow inward towards the valve cavity 165, and the valve wall 166 at the interior notch 158 may slightly bow outwards towards valve cavity 165. Additionally, the primary seal portion 140 may separate from the internal sealing edge 124.

As the medical implement 50 continues to exert axial force F onto the compressible valve 104, the medical implement 50 descends further into the inlet port 105, and due to the bowing of the external and internal notches 142 and 158 and the inwardly-recessed structure of the planar face 171, as the compressible valve 104 is further compressed, a moment M4 is created about a proximal end of the planar face 171 thereby causing the body portion 121 to buckle uniformly inward as illustrated in FIG. 5B. Since the body portion 121 buckles uniformly inward at the planar face 171, overfolding and/or folding overlaps of the valve wall 166 are prevented from occurring. The aforementioned configuration is advantageous over the currently existing valves of needless connectors, for example, as illustrated in FIG. 1A in that since folding overlaps of the valve wall 166 are prevented from occurring, the problematic pinch points— where normal forces traditionally develop which act against an internal moment caused by strain in the valve wall due to the deflected column and prevent the valve wall from freely opening during return—do not occur in the compressible valve 104. Advantageously, since the compressible valve 104 has minimal folding, upon removal of the axial force F, the valve wall 166 may freely expand and more quickly return to the uncompressed state illustrated in FIG. 5A as compared with the currently existing compressible valve 20 of FIG. 1A.

Figure 6B:
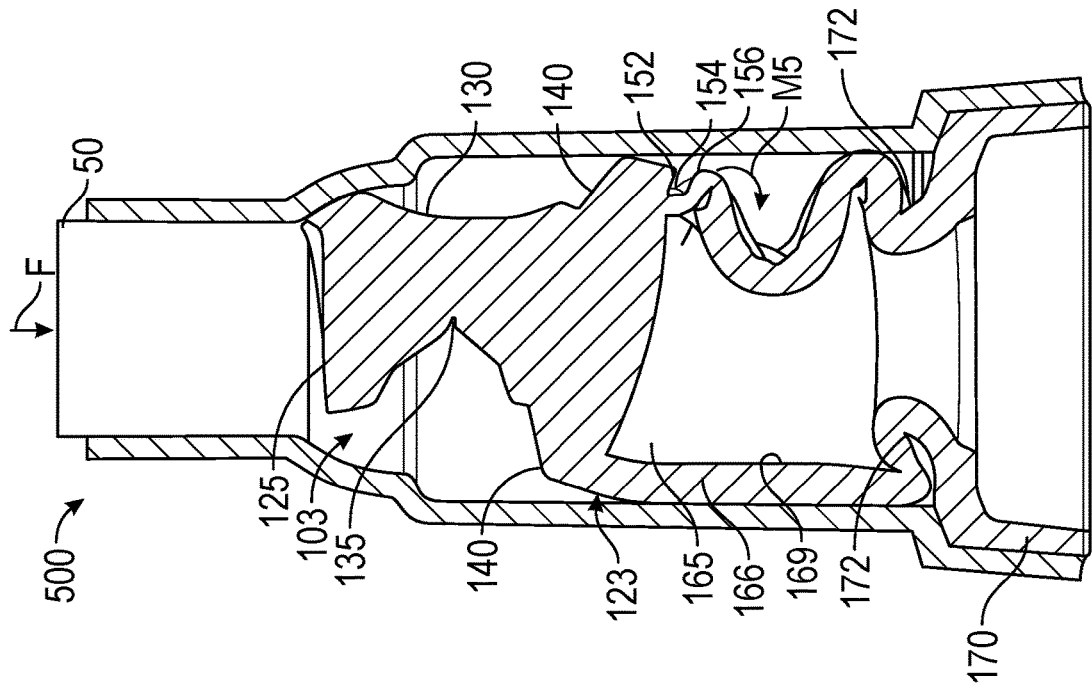
FIG. 6B illustrates a cross-sectional view of a needleless connector of FIG. 6A including the compressible valve subject to an axial force, in accordance with some embodiments of the present disclosure.
Figure 6A:
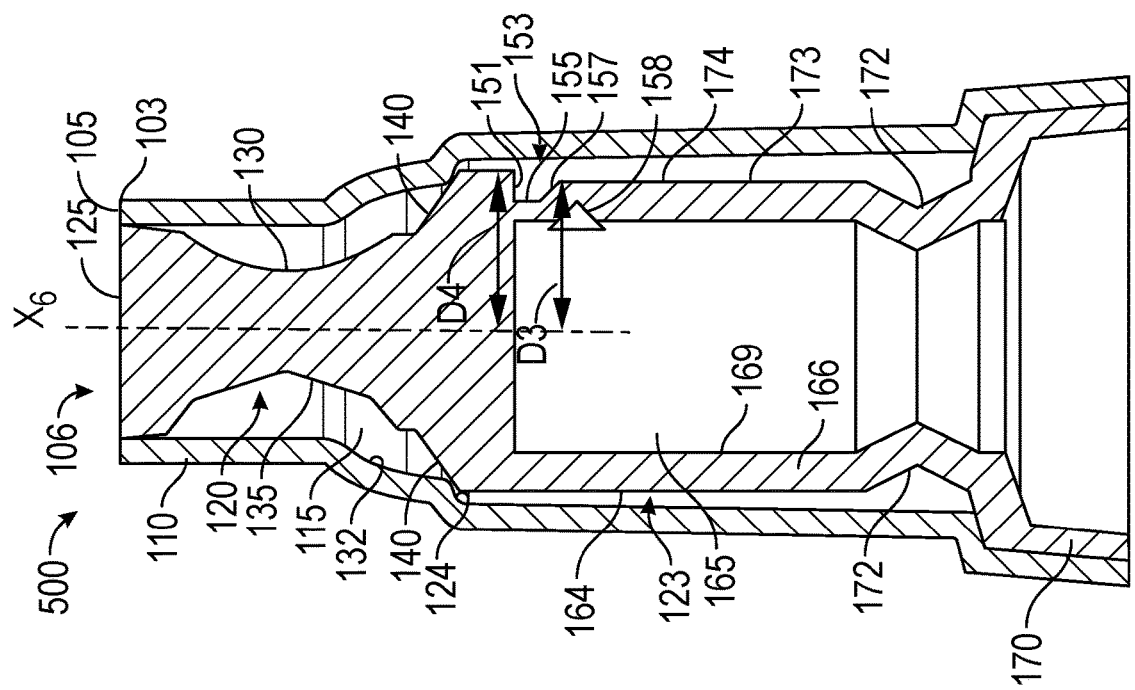
FIG. 6A illustrates a cross-sectional view of a needleless connector including compressible valve, in accordance with some embodiments of the present disclosure.

FIG. 6A illustrates a cross-sectional view of a needleless connector 500 including compressible valve 106, in accordance with some embodiments of the present disclosure. FIG. 6B illustrates a cross-sectional view of a needleless connector including the compressible valve 106 of FIG. 6A subject to an axial force F, in accordance with some embodiments of the present disclosure. In some embodiments, the compressible valve 106 of needleless connector 600 may have similar features and be similar in structure and function to the compressible valve 102 of needleless connector with a modification in the structure of the base portion 123. For example, referring to FIG. 6A, the needleless connector 500 may include the housing 110 and a compressible valve 102 disposed in the housing 110. The housing 110 has been described in detail above with respect to the needleless connector 100 of FIGS. 2A and 2C, therefore a detailed description thereof shall be omitted with respect to the needleless connector 500.

In some embodiments, an internal sealing edge 124 may be defined on the inner surface 132 of the housing 110. The internal sealing edge 124 may be a circumferential edge and configured for retaining the compressible valve 106 within the internal cavity 115 of the assembled needleless connector 500. In operation, the internal sealing edge 124 may be arranged to provide blocking of fluid flow in conjunction with a primary seal portion 140 of the compressible valve 102.

According to various embodiments of the present disclosure, the compressible valve 106 may include head portion 120, and flange portion 170 for securing the compressible valve 106 in the housing 110. The compressible valve 106 may further include a body portion 123 extending distally from the head portion 120 between the head portion 120 and the flange portion 170.

The head portion 120 and the flange portion 170 have been described in detail above with respect to the needleless connector 100 of FIGS. 2A and 2C, therefore a detailed description thereof shall be omitted with respect to the needleless connector 500. According to various embodiments of the present disclosure, the compressible valve 106 may have a longitudinal central axis $X_6$. In the non-activated state (e.g., in isolation or within the housing 110 but not displaced by medical implement 50) the longitudinal central axis $X_6$ may extend longitudinally through the head portion 120 and the body portion 123 of the compressible valve 106. In the aforementioned state, the body portion 123 of the compressible valve 106 may have the same axial center as the head portion 120 or other portions of the compressible valve 106. However, as described in further detail below, in an activated state (e.g., when the axial force F is applied to the compressible valve 106 using the medical implement or syringe 50) the longitudinal central axis $X_6$ of the compressible valve 106 may change and pivot in relation to the central longitudinal axis $X_1$ of the housing 110 upon the compressible valve 106 being activated by the medical implement or syringe 50.

In accordance with various embodiments of the present disclosure, the top section 125 of the head portion 120 may define a first or secondary seal portion 129 of the compressible valve 106. The body portion 123 may further define a second or primary seal portion 140 at a proximal end of the body portion 123. As depicted, the primary seal portion 140 may be disposed distally to the secondary seal portion 129.

In some embodiments, as illustrated in FIGS. 6A and 6B, the body portion 123 may include a cylindrical outer surface 164, an internal surface 168 that defines a valve cavity 165, and a wall 166 defined between the internal surface 168 and the outer surface 164. In some embodiments, the cylindrical outer surface 164 may include an external notch 153 extending along a portion of a circumference of the cylindrical outer surface 164. The external notch 153 has been described in detail above with respect to the needleless connector 200 of FIGS. 3A and 3B, therefore a detailed description thereof shall be omitted with respect to the needleless connector 500.

In accordance with various embodiments of the present disclosure, the compressible valve 102 may further include a planar face 174 extending distally from the external notch 153 and disposed between the external notch 153 and the flange portion 170. Accordingly, as illustrated, the planar face 174 may be recessed radially-inward relative to the outer circumferential surface 164.

In some embodiments, the compressible valve 106 may further include an internal notch 158 disposed on the internal surface 168 of body portion 123 and extending radially outward into the wall 166 towards the planar face 174. As depicted, a longitudinal position of the internal notch 158 along a length of the wall 166 may overlap at least in part with a longitudinal position of the external notch 153 along the length of the wall 166.

Similar to the embodiments of FIGS. 5A and 5B, the various embodiments of the present disclosure illustrated in FIGS. 6A and 6B are directed to advantageously providing a configuration in which the difference between the change in volume above the primary seal portion 140 and the change in the volume of the valve cavity 165 is expected to yield and maintain a uniform negative fluid displacement throughout insertion of the medical implement 50. Accordingly, the difference between the change in volume above the primary seal portion 140 and the change in the volume of the valve cavity 165 is expected to advantageously yield and maintain a uniform positive fluid displacement throughout removal of the medical implement as described in further detail below.

According to various embodiments of the present disclosure, as illustrated in FIGS. 6A and 6B, the body portion 123 of compressible valve 106 may further include a collapsible segment 172 extending along an entire outer perimeter 173 of the wall 166. The collapsible segment 172 may be recessed radially-inward from the wall 166. In some embodiments, the collapsible segment 172 may be disposed distally to the external notch 153. For example, as depicted, the collapsible segment 172 may be disposed at a distal and of the body portion 123 which may also correspond to the proximal end of the flange portion 170.

The collapsible segment 172 may be configured such that when an axial force F is applied to the head portion 120 of the compressible valve 106, the collapsible segment 172 collapses radially inward thereby causing downward (i.e., distal) displacement and/or vertical crushing/compressing of the compressible valve 106. Accordingly, due to the downward collapsing of the collapsible segment 172, the body portion 123 may first vertically crush/compress prior to buckling inward as illustrated in FIG. 6B. The configuration of the compressible valve 106 having the collapsible segment 172 on the body portion 123 is advantageous in achieving a more uniform negative displacement during initial insertion of the medical implement 50. This in turn allows for a more uniform positive volume displacement upon removal of the axial force F, thereby allowing the compressible valve 106 to more quickly spring back and expand to the uncompressed state illustrated in FIG. 6A as compared with the currently existing compressible valve 20 of FIG. 1A.

Additionally, the aforementioned configuration and structure of the compressible valve 106 with valve wall having internal and external notches 158 and 153, and the inwardly-recessed planar face 174 is advantageous in that when subject to an axial force, one side of the compressible valve 106 may buckle uniformly inward (as illustrated in FIG. 6B) to minimize folding overlaps or overfolding of the buckled valve wall 166, thereby maximizing response or rebound time of the compressible valve. In particular, in operation, when the axial force F is applied to the compressible valve 102, the compressible valve 106 may be compressed and buckle uniformly inward from a sealed configuration of the needleless connector 500 (illustrated in FIG. 6A) to an unsealed (open) configuration illustrated in FIG. 6B as described below.

In operation, as the medical implement 50 (e.g., a male luer, a syringe, or any similar medical implement) is initially inserted into the inlet port 105 of the needleless connector 500, an axial force F is exerted onto the compressible valve 106 such that the second notch 135 may fold or collapse and the first notch 130 may open or expand such that the top section 129 may tilt downwardly. In this regard, a fluid path from the medical implement 50 in the inlet port 105 may be established through the internal cavity 115 of the housing 110 to an outlet port of the housing 110. In some embodiments, the axial force F is exerted onto the compressible valve 106 such that the valve wall 166 at the exterior notch 153 may slightly bow inward towards the valve cavity 165, and the valve wall 166 at the interior notch 158 may slightly bow outwards towards valve cavity 165. Additionally, the primary seal portion 140 may separate from the internal sealing edge 124.

As the medical implement 50 continues to exert axial force F onto the compressible valve 106, the medical implement 50 descends further into the inlet port 105, and due to the bowing of the external and internal notches 153 and 158 and the inwardly-recessed structure of the planar face 174, as the compressible valve 106 is further compressed, a moment M5 is created about a proximal end of the planar face 174 thereby causing the body portion 123 to buckle uniformly inward as illustrated in FIG. 6B. Since the body portion 123 buckles uniformly inward at the planar face 174, overfolding and/or folding overlaps of the valve wall 166 are prevented from occurring. The aforementioned configuration is advantageous over the currently existing valves of needless connectors, for example, as illustrated in FIG. 1A in that since folding overlaps of the valve wall 166 are prevented from occurring, the problematic pinch points—where normal forces traditionally develop which act against an internal moment caused by strain in the valve wall due to the deflected column and prevent the valve wall from freely opening during return—do not occur in the compressible valve 106. Advantageously, since the compressible valve 106 has minimal folding, upon removal of the axial force F, the valve wall 166 may freely expand and more quickly return to the uncompressed state illustrated in FIG. 6A as compared with the currently existing compressible valve 20 of FIG. 1A.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A needleless connector, comprising:
a housing having a proximal end defining an inlet port of the housing, a distal end configured to be coupled with a base of the housing, and an inner surface defining an internal cavity extending between the proximal end and the distal end; and
a compressible valve disposed within the internal cavity, the compressible valve comprising a head portion, a flange portion for securing the compressible valve in the housing, and a body portion extending between the head portion and the flange portion, the body portion comprising:
a cylindrical outer surface including an external notch extending along a portion of a circumference of the cylindrical outer surface and recessed radially-inward from the cylindrical outer surface; and
a planar face extending distally from the external notch and disposed between the external notch and the flange portion,
wherein the planar face is recessed radially inward relative to at least a portion of the cylindrical outer surface.

2. The needleless connector of claim 1, wherein the compressible valve comprises an internal surface defining a valve cavity, a first wall section defined between the internal surface and the outer surface, and a second wall section defined between the internal surface and the planar face.

3. The needleless connector of claim 2, wherein the external notch comprises a first surface extending radially-inward from the cylindrical outer surface into the second wall section, a second surface extending longitudinally and distally from the first surface, and a ramp surface extending distally and radially outward from the second surface.

4. The needleless connector of claim 3, wherein the compressible valve comprises a longitudinal central axis, and a radial distance between a distal end of the ramp surface and the longitudinal central axis is less than a radial distance between a radially outward- most end of the first surface and the longitudinal central axis.

5. The needleless connector of claim 2, further comprising an internal notch disposed on the internal surface and extending radially outward into the second wall section towards the planar face.

6. The needleless connector of claim 5, wherein a position of the internal notch along a length of the wall overlaps at least in part with a position of the external notch along a length of the second wall section.

7. The needleless connector of claim 1, wherein the head portion comprises at least one notch disposed along an exterior of the head portion.

8. A needleless connector, comprising:
a housing having a proximal end defining an inlet port of the housing, a distal end configured to be coupled with a base of the housing, and an inner surface defining an internal cavity extending between the proximal end and the distal end; and
a compressible valve reciprocally disposed within the internal cavity, the compressible valve comprising a head portion and a body portion extending distally from the head portion, the body portion comprising:
a cylindrical outer surface including a cutout extending longitudinally along the cylindrical outer surface and recessed radially-inward from the cylindrical outer surface, the cutout comprising a ramp surface.

9. The needleless connector of claim 8, wherein the compressible valve comprises an internal surface defining a valve cavity, a first wall section defined between the internal surface and the outer surface, and a second wall section defined between the internal surface and the ramp surface.

10. The needleless connector of claim 9, wherein the cutout comprises a first surface recessed radially-inward from the cylindrical outer surface, and the ramp surface extends distally and radially outward from the first surface.

11. The needleless connector of claim 10, wherein the ramp surface comprises a planar surface.

12. The needleless connector of claim 10, wherein the compressible valve further comprises a flange portion for securing the compressible valve in the housing, and the ramp surface extends from the first surface to the flange portion.

13. The needleless connector of claim 12, wherein opposing sides of the ramp surface are angled outwardly away from each other at the first surface, and angled inwardly towards each other at the flange portion.

14. The needleless connector of claim 10, wherein the compressible valve further comprises secondary cutouts extending longitudinally along the cylindrical outer surface and recessed radially-inward from the cylindrical outer surface.

15. The needleless connector of claim 14, wherein the secondary cutouts are disposed on opposing sides of the ramp surface of the cutout.

* * * * *